United States Patent [19]

Manning et al.

[11] Patent Number: 4,968,142

[45] Date of Patent: Nov. 6, 1990

[54] CLOSED INDUCTIVELY COUPLED PLASMA CELL

[75] Inventors: Thomas J. Manning, Gainesville, Fla.; Byron A. Palmer, Los Alamos; Douglas E. Hof, Santa Fe, both of N. Mex.

[73] Assignee: The United States of America as represented by the United States Department of Energy, Washington, D.C.

[21] Appl. No.: 360,559

[22] Filed: Jun. 2, 1989

[51] Int. Cl.[5] .................... G01N 21/73; G01N 31/12; G01J 3/443
[52] U.S. Cl. .................................. 356/316; 436/155; 315/111.41
[58] Field of Search .............. 356/315, 316, 346; 219/121.48; 204/155, 164; 315/39, 248, 111.41; 333/24 C, 99 PR; 436/155

[56] References Cited

U.S. PATENT DOCUMENTS

| | | | |
|---|---|---|---|
| 4,266,166 | 5/1981 | Proud et al. | 315/248 |
| 4,473,736 | 9/1984 | Bloyet et al. | 219/121 PM |
| 4,482,246 | 11/1984 | Meyer et al. | 356/316 |
| 4,532,219 | 7/1985 | Hagen et al. | 436/155 |

Primary Examiner—Vincent P. McGraw
Assistant Examiner—LaCharles P. Keesee
Attorney, Agent, or Firm—Ray G. Wilson; Paul D. Gaetjens; William R. Moser

[57] ABSTRACT

A closed inductively coupled plasma cell generates a relatively high power, low noise plasma for use in spectroscopic studies. A variety of gases can be selected to form the plasma to minimize spectroscopic interference and to provide a electron density and temperature range for the sample to be analyzed. Grounded conductors are placed at the tube ends and axially displaced from the inductive coil, whereby the resulting electromagnetic field acts to elongate the plasma in the tube. Sample materials can be injected in the plasma to be excited for spectroscopy.

4 Claims, 1 Drawing Sheet

CLOSED INDUCTIVELY COUPLED PLASMA CELL

This invention is the result of a contract with the Department of Energy (Contract No. W7405ENG36).

BACKGROUND OF INVENTION

This invention generally relates to spectroscopic studies and, more particularly, to inductively coupled Plasma tubes used for sample excitation and spectroscopic studies.

Plasma discharges are frequently used to heat a sample material for spectroscopic studies. The spectra of the known plasma gas can be subtracted from the overall spectrum in order to derive the sample spectrum. Plasma heating requires a relatively high-power Plasma and a plasma with little noise is required to isolate the sample spectrum. Flowing gas streams have been inductively heated to generate plasmas effective to atomize, ionize and/or excite sample materials for mass spectroscopy studies, where typical plasma temperatures are in the range of 4,000 to 10,000 K.

While argon and helium are conventional gases used in such inductively coupled (ICP) plasmas, other gases may be selected for noninterference with the expected sample spectrum i.e.,. gases such as neon, xenon, krypton, hydrogen, nitrogen, oxygen, carbon dioxide, and ethylene. The capability of selecting from a variety of gases to form the plasma enables the plasma density and temperature range, which are inversely proportional to the ionization potential of the gas, to be varied. It will be appreciated, however, that a plasma jet of some gases, e.g., hydroger, can be dangerous or may consume quantities of expensive gases i.e., xenon. Illustrative Plasma generators are discussed in U.S. Pat. No. 4,473,736. "Plasma Generator", issued September 25, 1984, to Bloyet et al.. and 4,482.246. "Inductively Coupled Plasma Discharge in Flowing Non-Argon Gas at Atmospheric Pressure for Spectrochemical Analysis." issued Nov. 13, 1984, to Meyer et al.

Electrodeless discharge lamps provide a relatively low noise light source and have been used in some spectroscopic systems. However such lamPs generally operate at low power and cannot always be used in spectroscopic studies. A discussion of electrodeless discharge lamps and other conventional discharge devices is found in U.S. Pat. 4,266,166, "Compact Fluorescent Light Source Having Metallized Electrodes," issued May 5, 1981 to proud et al.

In accordance with the present invention an inductively coupled plasma is generated in a closed torch for operation at relatively high power (i.e. up to about 1 kw) and low noise for application to a variety of spectroscopic studies. Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention may comprise a static closed end inductively coupled plasma cell. A tube, containing a gas which forms the plasma, has a coil disposed around the tube for inductively exciting the gas for forming the plasma. At least one grounded conductor is provided on the tube, axially spaced from the inductive coil on the tube for elongating the plasma in the tube. No gas flow is required to the tube since the elongated plasma enables a high power input to the inductive coil where the plasma is not concentrated adjacent the coil.

BRIEF DESCRIPTION OF THE DRAWINGS

The accompanying drawing, which is incorporated in and forms a part of the specification, illustrates an embodiment of the Present invention and, together with the description, serve to exPlain the PrinciPles of the invention. In the drawings.

DETAILED DESCRIPTION OF THE INVENTION

Figure 1:
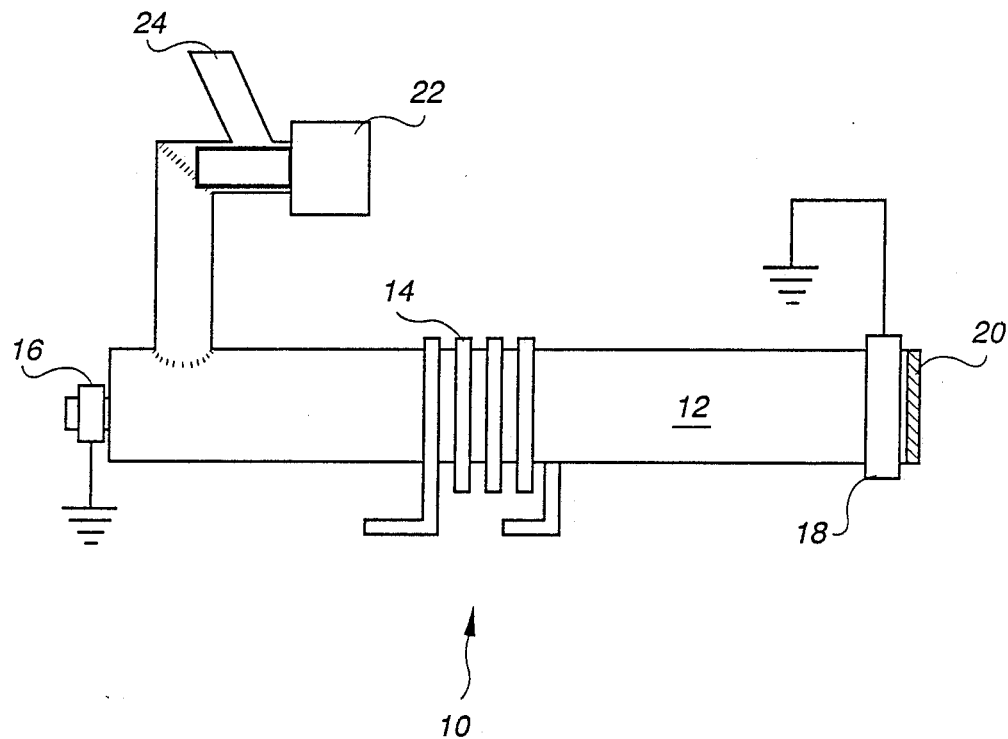
FIG. 1 is a pictorial illustration of a Plasma tube according to the Present invention.

Referring now to FIG. 1, there is depicted a static, closed end plasma cell 10 according to the present invention. Plasma tube 12 encloses a gas seiected to form the plasma for spectroscopic studies. Coil 14 is provided about tube 12 for inductively couPling radio-frequency (rf) energy to the gas within tube 12. In a conventional plasma tube, plasma would be generated in the gas adjacent coil 14 and would be conducted along tube 12 by the flowing gas.

As shown in FIG. 1, tube 12 is closed at both ends to form a contained volume for the Plasma. Accordingly. it is a feature of the Present invention to elongate the plasma axially along tube 12 by including grounded conductors 16 and 18 about the ends of the volume in which the plasma is desired. Thus, at least one of the grounded conductors 16, 18 is required to spread the plasma flow and both grounded conductors 16, 18 are used to elongate the plasma over the entire tube length. Grounded conductors 16, 18, establish an electromagnetic field boundary with inductive coil 14, within which volume the plasma can exist.

In application to spectroscopic studies, stopcock 22 and inlet 24 are provided for introducing a plasma gas and a sample material within tube 12. As the sample material is excited by the plasma within tube 12, the light output may be provided through quartz window 20 for input to a spectrometer. For possible application to mass spectrometers, one end of tube 12 may be gated to a mass spectrometer (not shown) to release the excited plasma into the low pressure environment, i.e., pressures less than about $10^{-5}$ torr for ion detection.

In one embodiment, closed cell 10 was constructed according to the above description. Quartz tube 12 was provided with a 17 mm OD. 15 mm ID. and 14 cm length. Grounded clips 16, 18 were provided on each end of tube 12 and window 20 enabled end-on viewing of the excited sample. Coil 14 was a four-turn coil formed of gold-plated ⅛ in. copper tubing. Coil 14 was excited at 27.12-MHz by a power supply available as RF Plasma Products HFP 5000-D(5 kW). A plasma was initiated by turning on the rf field and slowly increasing the power. Where necessary at high pressures (e.g., 10–100 torr), a tesla coil discharge was provided through one of the grounded conductors 16, 18 to ignite the plasma. Nitrogen was blown across cell 10 for cooling purposes.

Using cell 10 depicted in FIG. 1 plasmas were generated in a variety of gases. As shown in Table I, plasmas were initiated in xenon, neon, argon, krypton, helium, hydrogen, nitrogen, oxygen, carbon dioxide and ethylene. The input power and plasma temperature are illustrated in Table I. Where a Na D-line was obtained from impurities in the quartz, a doppler temperature was obtained for the plasma. The pressure and power values shown in Table I are illustrative only and may be adjusted for the particular specimen being analyzed. Further, while the gases listed in Table I are exemplary, it is expected that closed plasma cell 10 can generate plasmas using atomic species which are gaseous at low pressure (mercury, radon- volatile salts), diatomic gases (NO, CO, etc.), and Polyatomic gases ($NO_2$, $SO_2$, $C_2H_2$, and other hydrocarbons).

Thus an inductively coupled plasma cell is hereinabove described for use in spectroscopic studies. By providing a contained plasma volume, hydrogen and other explosives gases may be used with relative safety. Further, expensive gases. such as xenon, are not consumed in the plasma excitation process. A closed system plasma may be provided at pressures up to 100 torr and at powers at least up to 1 kW. The closed ICP cell may replace electrodeless discharge lamPs in various applications. particularly where an increased Plasma Power is desired. For spectroscopic applications the closed ICP cell herein described provides a relatively high temperature for sample excitation with relatively low noise. Plasma may be produced from a variety of gases and the cell provides a reservoir of excited atoms and molecules which are stable in the plasma environment.

TABLE I

| Plasma | Plasm-generated parameter used and calculated Doppler temperature for each | | | |
|---|---|---|---|---|
| | Pressure | Power | Element/Line | Temperature |
| Xenon | 7 torr | 250 W | Na/16973 $cm^{-1}$ (589.0 nm) | 3689 K |
| | | | Xe/21401 $cm^{-1}$ (467.3 nm) | 5175 K |
| Neon | 6 torr | 75 W | Ne/15615 $cm^{-1}$ (640.4 nm) | 732 K |
| Argon | 6 torr | 100 W | Ar/12318 $cm^{-1}$ (881.8 nm) | 1714 K |

TABLE I-continued

| Plasma | Plasm-generated parameter used and calculated Doppler temperature for each | | | |
|---|---|---|---|---|
| | Pressure | Power | Element/Line | Temperature |
| Krypton | 6 torr | 250 W | Na/16973 $cm^{-1}$ (589.0 nm) | 2820 K |
| Helium | 6 torr | 100 W | — | — |
| Hydrogen | 6 torr | 400 W | Na/16973 $cm^{-1}$ (589.0 nm) | 3240 K |
| Nitrogen | 1.5 torr | 300 W | Na/16956 $cm^{-1}$ (589.6 nm) | 4680 K |
| Oxygen | 6 torr | 550 W | Na/16973 $cm^{-1}$ (589.0 nm) | 2430 K |
| Carbon Dioxide | 2.8 torr | 250 W | Na/16973 $cm^{-1}$ (589.0 nm) | 2430 K |
| Ethylene | 2.1 torr | 500 W | Na/16973 $cm^{-1}$ (589.0 nm) | 2800 K |

The foregoing description of the preferred embodiment of the invention have been presented for purposes of illustration and description. It is not intended to be exhaustive or to limit the invention to :he precise form disclosed, and obviously many modifications and variations are possible in light of the above teaching. The embodiment as chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A closed end inductively coupled plasma cell, comprising:
   a tube for containing a gas which forms said plasma;
   a coil disposed around said tube for inductively exciting said gas for forming said plasma; and
   at least one grounded conductor on said tube and axially spaced from said coil on said tube for elongating said plasma in said tube.

2. An inductively coupled plasma cell according to claim 1 wherein said at least one grounded conductor is a grounded conductor adjacent each end of said tube.

3. An inductively coupled plasma cell according to claim 2, further including a quartz window adjacent one end of said tube for light output for spectroscopic analysis.

4. An inductively coupled plasma cell according to claim 2, wherein said gas is selected from the group consisting of xenon, neon, arqon, krypton, helium. hydrogen, nitrogen, oxygen, carbon dioxide, and ethylene.

* * * * *